United States Patent [19]

Rubin et al.

[11] Patent Number: 5,498,519
[45] Date of Patent: Mar. 12, 1996

[54] HYPOTHERMIC PRESERVATION OF MAMMALIAN HEARTS BY BLOCKING THE $NA^+/K^+/CL^-$ CO-TRANSPORTER USING THE CO-TRANSPORTER BLOCKER, FUROSEMIDE

[75] Inventors: Yoram Rubin, Tel Aviv; Gil Navon, Ramat Gan, both of Israel

[73] Assignee: Ramot-University Authority for Applied Research and Industrial Development Ltd., Tel Aviv, Israel

[21] Appl. No.: 310,371

[22] Filed: Sep. 22, 1994

Related U.S. Application Data

[63] Continuation of Ser. No. 99,711, Jul. 29, 1993, abandoned.
[51] Int. Cl.$^6$ .............................. A01N 1/02; A01N 43/38; A01N 43/08; A01N 41/02
[52] U.S. Cl. ........................... 435/1.2; 514/409; 514/461; 514/518
[58] Field of Search .............................. 435/1; 514/461, 514/518, 409

[56] References Cited

PUBLICATIONS

Askenasy N et al., "Sodium ion transport in rat hearts during cold ischemic storage", *Magn. Reson. Med.*, 1992, 28:249–263.

Pike MM et al., "$^{23}$Na NMR measurements of intracellular sodium in intact perfused ferret hearts during ischemia and reperfusion", *Am. J. Physiol*, 1990, 259:H1767–H1773.

Geck, P et al., "The Na–K–2Cl Cotransport system", *J. Membrane Biol.*, 1986, 91:97–105.

Pike MM et al., "$^{23}$Na and $^{39}$K nuclear magnetic resonance studies of perfused rat hearts", *Biophys. J.*, 1985, 48:159–173.

Ledingham S et al., "The St. Thomas' Hospital cardioplegic solution", *J. Thorac. Cardiovasc. Surg.*, 1987, 93:240–246.

Christlieb Iy et al, J Thoraac Cardin Vase Surg. 84:689–95 (1982).

Borchgrevink PC et al, Pharmacology and Toxicology 64:100–106 (1989).

*Primary Examiner*—Marian C. Knode
*Assistant Examiner*—Sandra Saucier
*Attorney, Agent, or Firm*—Kohn & Associates

[57] ABSTRACT

A method for preserving mammalian hearts while under ischemic conditions is accomplished by exposing the heart to a preservation solution containing a pharmacologically effective concentration of a $Na^+/K^+/Cl^-$ co-transporter blocker agent, such as Furosemide, Bumetanide or Piretanide, thereby extending survival of the heart.

2 Claims, 2 Drawing Sheets

HYPOTHERMIC PRESERVATION OF MAMMALIAN HEARTS BY BLOCKING THE NA+/K+/CL− CO-TRANSPORTER USING THE CO-TRANSPORTER BLOCKER, FUROSEMIDE

This is a continuation of application Ser. No. 08/099,711 filed on Jul. 29, 1993, abandoned.

TECHNICAL FIELD

This invention relates to the preservation of hearts during ischemic conditions, such as donor hearts for transplantation during transport and hearts during an open heart surgery.

BACKGROUND ART

The success of heart transplantation depends upon satisfactory function of the new heart after implantation in the recipient. One factor contributing to a successful transplant is heart preservation while it is ex vivo, that is while it is being transported from the donor to the recipient. It is rare, indeed, that a donor and recipient will be at the same medical facility. Therefore, the ability to preserve donor hearts while transporting them long distances is crucial to successful heart transplantations.

In recent years, extensive studies have been conducted toward extension of heart preservation. To date, however, preservation ability is on the order of four to five hours using cold ischemic preservation. Longer safe preservation times would greatly increase the number of potential donor hearts.

Moreover, open heart surgery has become a common major surgery in the western world. During this operation, the heart is disconnected from the blood supply (i.e, under ischemia). In order to be preserved during the operation, a cold cardioplegic solution is infused into the heart. However, to date, this preservation is limited to about two hours before irreversible damage to the heart is caused.

During the past decade, St. Thomas' Hospital (ST) cardioplegic solution has been used routinely in heart transplantation programs and in open heart surgery.

It was recently shown that under hypothermic ischemic conditions (hypothermic condition without any infusion of perfusate), myocardial intracellular concentration of $Na^+$ is markedly increased. (Askenasy et al , "Sodium ion transport in rat hearts during cold ischemic storage", *Magn. Reson. Med.*, 1992, 28:249–263; Pike et al., "$^{23}$Na NMR measurements of intracellular sodium in intact perfused ferret hearts during ischemia and reperfusion", *Am. J. Physiol*, 1990, 259:H1767–H1773; and Pike et al , "$^{23}$Na and $^{39}$K nuclear magnetic resonance studies of perfused rat hearts", *Biophys J.*, 1985, 48:159–173). This intracellular $Na^+$ accumulation may lead to intracellular accumulation of water, followed by an increase in cell volume and mitochondrial swelling and to an increase in intracellular $Ca^{++}$ concentration via the $Na^+/Ca^{++}$ exchanger and eventually to cell death.

Furosemide is a loop diuretic agent, commonly used in the treatment of hypertensive patients. A diuretic is a substance that increases the rate of urine output. Most diuretics act by decreasing the rate of reabsorption of fluid from the tubules, reducing the total amount of fluid in the body. The loop diuretic agents are known to block the $Na^+/K^+/Cl^-$ co-transporter, and called such because they were first discovered as blockers of the reabsorption of sodium and chloride ions from the ascending limb in the loop of Henle in the kidney.

Applicants discovered that under hypothermic conditions, as in the hypothermic preservation of the heart, the $Na^+/K^+/Cl^-$ co-transporter located in the sarcolemma (Geck et al., "The Na-K-2Cl Contrasport system", *Journal Membrane Biol.*, 1986, 91:97–105) plays a major role. Due to the decrease in temperature and the lack of energy supply, the Na/K ATPase is inactive causing a large amount of Na+ to permeate into the cell. This intracellular accumulation of $Na^+$ can be markedly blocked by the administration of the $Na^+/K^+/Cl^-$ blockers, such as furosemide, bumetanide, or piretanide, protecting the myocardial tissue during the preservation time.

SUMMARY OF THE INVENTION AND ADVANTAGES

According to the present invention, a method for preserving mammalian hearts while under ischemic conditions is accomplished by administering to the heart a preservation solution including a pharmacologically effective concentration of a $Na^+/K^+/Cl^-$ co-transporter blocker to extend survival of the heart.

This inventive protocol extends the survival rate of the heart to at least eight hours after removal from the donor, adding at least four hours to the current ex vivo survival time under hypothermic conditions, as well as extending survival to in vivo ischemic hearts during open heart surgery.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
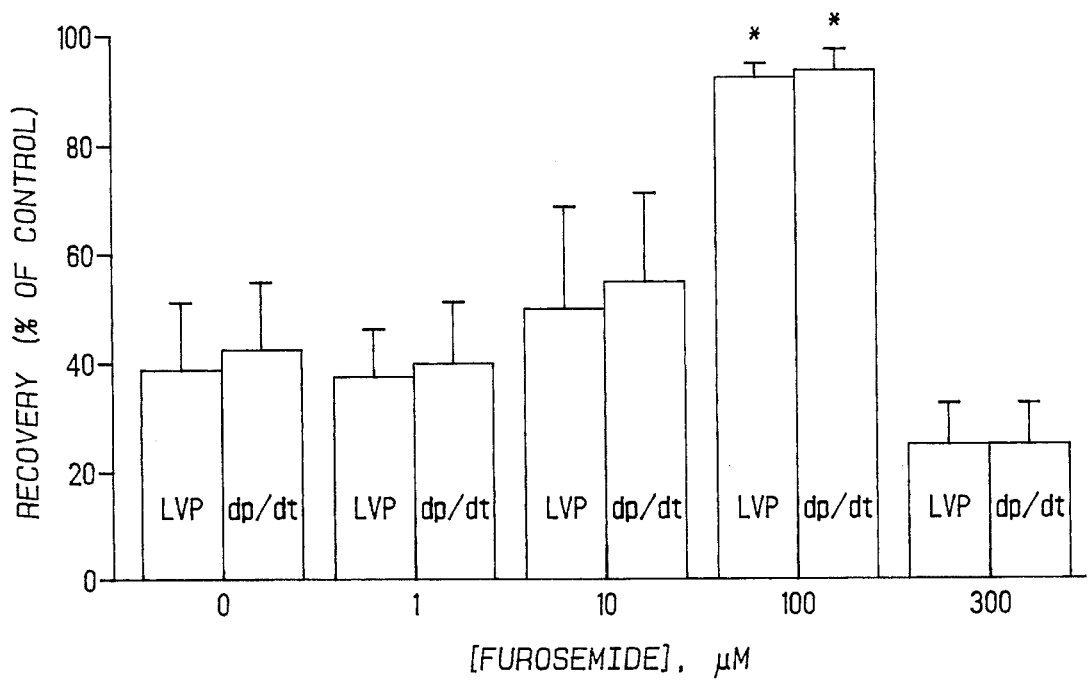
FIG. 1 is a bar graph showing mechanical recovery after eight hours of hypothermic ischemia (4° C.) using ST cardioplegic solution as a function of the furosemide concentration. LVP=left ventricular pressure. dp/dt=left ventricular pressure derivative. Number of experiments were n=6,5,4,5 and 5 for furosemide concentrations of 0, 1, 10, 100 and 300 mM, respectively. *p<0.01.

According to the present invention, a method is disclosed for extending preservation of mammalian hearts under ischemic conditions, such as while ex vivo during transplantation and during open heart surgery. This is accomplished by first infusing a preservation solution containing a pharmacologic effective concentration of the $Na^+/K^+/Cl^-$ co-transporters blockers such as furosemide, bumetanide and piretanide. The administration of the blockers can be followed by an infusion of a cold cardioplegic solution containing the same agent which is followed by bathing the heart in a cardioplegic solution containing the same agent. In the preferred embodiment, the cardioplegic solution is St. Thomas' Hospital solution (ST).

Under hypothermic conditions, as in the hypothermic preservation of the heart, the $Na^+/K^+/Cl^-$ co-transporter located in the sarcolemma (Geck et al., "The Na-K-2Cl Contrasport system", *J. Membrane Biol.*, 1986, 91:97–105) plays a major role. Due to the decrease in temperature and the lack of an energy supply, the Na/K ATPase is inactive causing a large amount of $Na^+$ to permeate into the cell. This intracellular accumulation of $Na^+$ can be markedly blocked by the administration of the $Na^+/K^+/Cl^-$ blockers, such as furosemide, bumetanide, or piretanide, protecting the myocardial tissue during the preservation time.

The present invention requires the in vivo infusion of a preservation solution including a pharmacologically effective concentration of $Na^+/K^+/Cl^-$ co-transporters blocker such as furosemide, bumetanide or piretanide. This can be followed by infusing the heart with a cardioplegic solution containing the pharmacologically effective concentration of the $Na^+/K^+/Cl^-$ co-transporters blocker, and bathing it with the same solution. This is done since the $Na^+/K^+/Cl^-$ co-transport system plays a major role in the regulation of $Na^+$ influx under 4° C. hypothermic preservation. However, other mechanisms of action may be operative in this system which are not related to $Na^+$ accumulation or $Na^+/K^+/Cl^-$ transport. Also, the heart may be maintained at non-hypothermic temperatures.

The dose response study (FIG. 1) indicates that 100 μM furosemide is an effective dose to preserve the mechanical recovery of the heart. On the other hand, 1000 μM furosemide appears to bring about no recovery. Therefore, it appears that in mammals, the effective dose should be below 500 μM. Alternatively, 0.1 μM to 10 μM of bumetanide or 0.1 μM to 100 μM of piretanide can be administered.

The invention can be readily used by adding the co-transport blocker to the perfusate given before the removal of the heart, and to the cardioplegic solution. It can be added by the manufacturer, giving the user solutions that already contain the co-transport blocker, or it can be produced as a separate ampoule containing the co-transport blocker that can be added by the user to the appropriate solution.

The following example illustrates the application of the present invention:

Materials and Methods

Male sprague-dawley rats, weighing 300–400 g., were anesthetized with phenobarbital sodium (20 mg/rat, ip). Hearts were excised and placed immediately in iced heparinized saline. After cession of contractions, the aortas were cannulated for a Langendorff perfusion system at 37° C. with a modified phosphate-free Krebs-Henseleit (KH) bicarbonate buffer solution at a pressure of 95 cm water for five minutes. Then, the perfusate was changed to KH with furosemide (Sigma Chemical Co., St. Louis, Mo., USA) and the hearts were paced (Harvard stimulator, Harvard apparatus LD) for 15 minutes. After this period, the hearts were perfused with ST cardioplegic solution with furosemide at 4° C. for five minutes in which cessation of contraction was achieved. Then, the hearts were placed in ST cardioplegic solution with furosemide at 4° C. for eight hours. The control group underwent the same protocol, but without furosemide. Furosemide was used in the following concentrations: 1 μM, 10 μM, 100 μM, 300 μM, and 1000 μM. At the end of the preservation time, the hearts (treated, and not treated) were reperfused with KH without furosemide at 37° C. in the Langendorff perfusion system, and after the initiation of spontaneous contractions, they were paced at the same rate as at the pre-ischemic period for 30 minutes.

The KH solution contained the following components: 121 mM NaCl, 5.9 mMKCl, 1.75 mM $CaCl_2$, 1.2 mM $MgSO_4$, 23 mM $NaHCO_3$ and 11 mM glucose. The solution was bubbled continuously with a mixture of 95% oxygen and 5% carbon dioxide, and the pH was 7.4.

The ST cardioplegic solution contained the following components: 110 mM NaCl, 16 mM KCl, 16 mMM$gCl_2$, 1.2 mM$CaCl_2$, 10 mM$NaHCO_3$, and the pH was 7.8. (Ledingham et al., "The St. Thomas' Hospital cardioplegic solution", *J. Thorac. Cardiovasc. Surg.*, 1987, 93:240–246).

Ventricular pressure was measured by a transducer, connected by a polyethylene tube to a thin latex balloon, which was inserted into the left ventricle across the mitral valve. The balloon was inflated with an aqueous solution to achieve an initiated end diastolic pressure of 10–15 mmHg, and was then kept isovolumic (Isovolumic=Equal volume) throughout the experiment. Left ventricular pressure and dp/dt were recorded simultaneously on a multichannel recorder (Gould recorder, model 1402).

Values presented are mean ±SEM. Statistical significance was determined with Student's test for unpaired observation, and a value of $P<0.05$ was considered significant.

Example

The effect of furosemide (1–1000 μM) on preservation of rat hearts using ST cardioplegic solution under hypothermic conditions was studied. Recovery was evaluated using Langendorff perfusion with Krebs-Henseleit solution and pressure measurement with a latex balloon.

The effect of various concentrations of furosemide on the left ventricular pressure (LVP) and dp/dt recoveries of rat hearts preserved in ST cardioplegic solution for eight hours at 4° C. is shown in FIG. 1. As seen in the figure, while no effect at furosemide concentration of 1 μM was observed, some effect, though not statistically significant, was observed at a concentration of 10 μM furosemide. A very large and statistically significant effect ($p<0.01$) was observed in the presence of 100 μM furosemide. A further increase in the furosemide concentration to 300 μM caused a significant decrease in the recoveries of LVP and dp/dt accompanied by occasional arrhythmia. At a concentration of 1000 μM furosemide, no recovery was observed.

Figure 2:
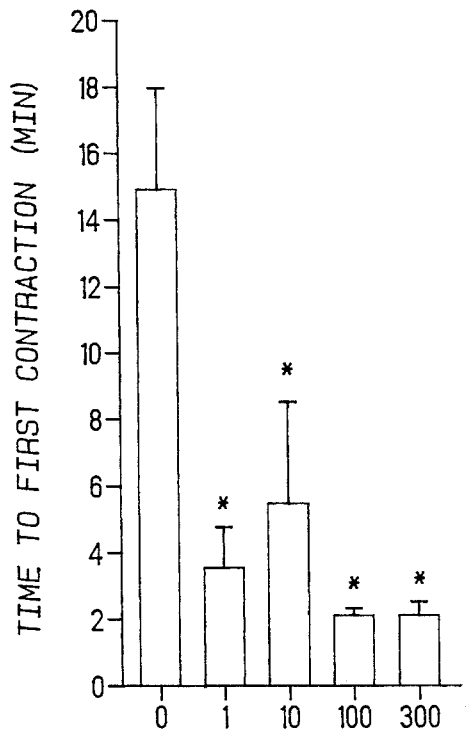
FIG. 2 is a bar graph showing the time elapsed until the first recorded myocardial contraction upon reperfusion of the same heart as in FIG. 1 as a function of furosemide concentrations. *p<0.01.

Another effect of furosemide was a shortening of the time elapsed between the initiation of the reperfusion and the first spontaneous recorded contraction. The results are shown in FIG. 2. It is interesting to note that this effect was very significant, even at the lowest furosemide concentration of 1 μM.

A significant effect of furosemide added to the ST cardioplegic solution was found in two parameters: (a) the mechanical recovery measured by both LVP and dp/dt; and (b) the time that elapsed until the first contraction upon reperfusion. While the improvement of the mechanical recovery was significant only at a concentration of 100 μM, that of the time elapsed until the first contraction was already significant at a furosemide concentration of 1 μM.

Further, applicants found in an ultrastructural electron microscopy study that in hearts treated with 100 μM furosemide, the mitochondrial volume is significantly reduced as opposed to the untreated hearts, indicating the protective effect of the co-transporter blocker, such as furosemide.

Figure 3:
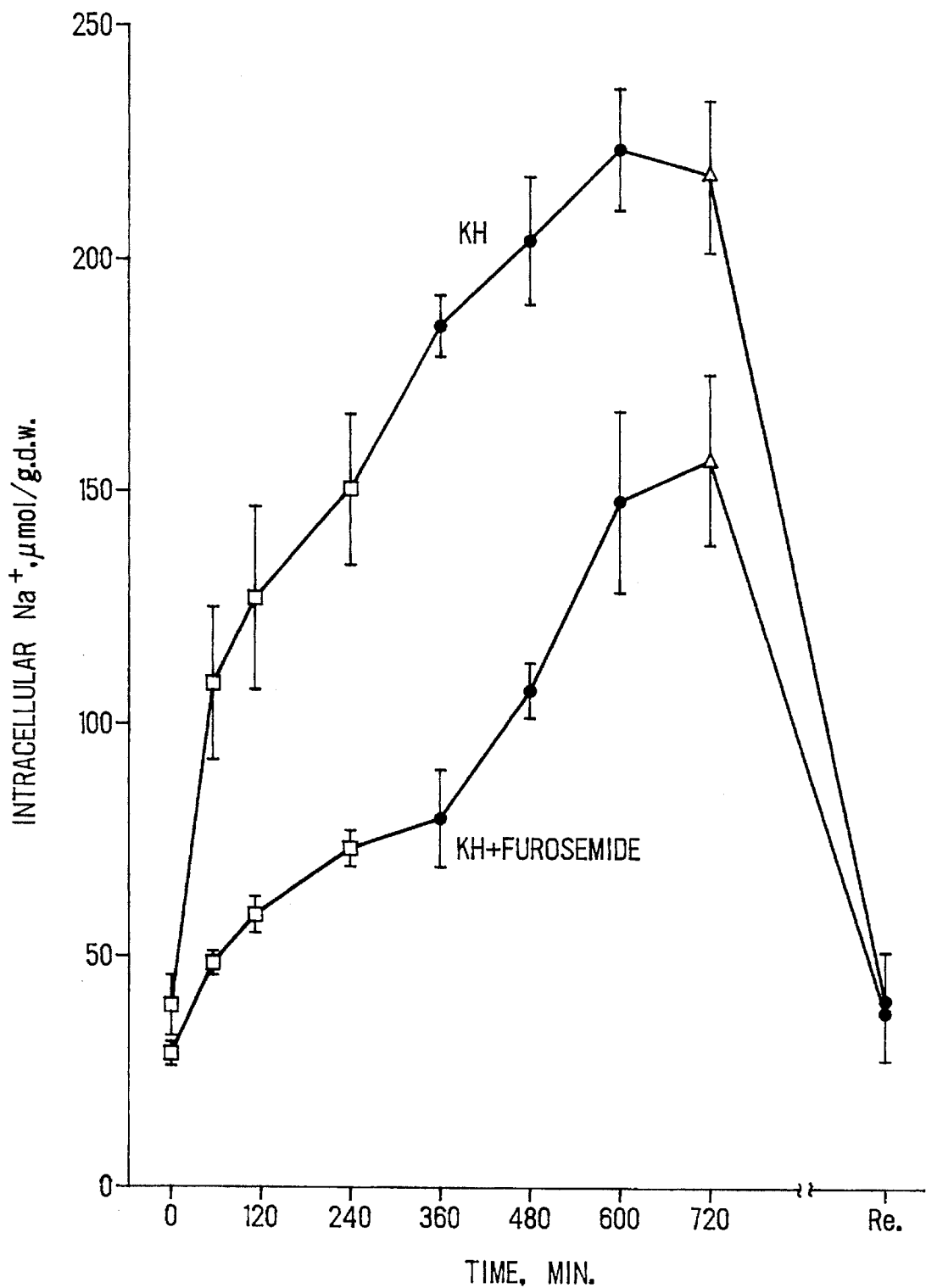
FIG. 3 is a graph showing the effect on intracellular sodium influx of heart tissue in KH, with and without the addition of Furosemide, the results expressed as mean ±standard error, for □ n=7; • n=5; ∆ n=6.

A $^{23}Na$ NMR study that furosemide at concentrations as low as 1 μM inhibits markedly the sodium ions influx into the myocardial cells during preservation of rat hearts at 4° C.

in KH solution is shown in FIG. 3. It is possible that the time elapsed until the first contraction upon reperfusion is the period that is needed by the myocardial cells to pump out $Na^+$ and other ions in order to recover the membrane potential. Thus, it is reasonable to assume that furosemide affects the sinoatrial node cells at very low concentrations. On the other hand, the recovery of the LVP and dp/dt, although they may also be dependent on the ion flux, may be related to irreversible damage to various intracellular organelles such as the mitochondria.

The present invention demonstrates that the Furosemide-sensitive $Na^+/K^+/Cl^-$ co-transport system plays a major role in the regulation of $Na^+$ influx under 4° C. hypothermic preservation. The above data demonstrate the beneficial effect on the recovery of hearts preserved in cardioplegic solution with the addition of furosemide under hypothermic conditions.

In the presence of an effective concentration of furosemide, the recoveries of the left ventricle pressure and the dp/dt after eight hours of hypothermic ischemia at 4° C. were 93% (±3.5%) and 93.5% (±4.5%) of the pre-ischemic hearts, respectively. The recoveries without the addition of furosemide were 39% (±11%) and 42% (12%), respectively. A range of effective furosemide concentrations were determined. In an effective concentration range of 1–300 μM, furosemide shortened significantly the time elapsed until the first recorded myocardial contraction upon reperfusion.

Furosemide appears to improve the recovery by blocking the sarcolemmal $Na^+/K^+/Cl^-$ co-transport system, and thereby reducing the myocardial injury caused by intracellular $Na^+$ accumulation during hypothermic ischemia.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

REFERENCES

1. Askenasy N et al,. "Sodium ion transport in rat hearts during cold ischemic storage", *Magn. Reson. Med.,* 1992, 28:249–263
2. Pike MM et al., "$^{23}$Na NMR measurements of intracellular sodium in intact perfused ferret hearts during ischemia and reperfusion", *Am. J. Physiol,* 1990, 259:H1767–H1773
3. Pike MM et al., "$^{23}$Na and $^{39}$K nuclear magnetic resonance studies of perfused rat hearts", *Biophys. J.,* 1985, 48:159–173
4. Geck, Pet al., "The Na-K-2Cl Cotransport system" *J. Membrane Biol* , 1986, 91:97–105
5. Ledingham S et al., "The St Thomas' Hospital cardioplegic solution", *J. Thorac. Cardiovasc. Surg.,* 1987, 93:240–246.

What is claimed is:

1. A process for preserving mammalian hearts prior to transplantation comprising the steps of:
    a) perfusing the heart with a preservation solution comprising furosemide in a concentration of about 100 μM;
    b) perfusing the heart with a cardioplegic solution comprising furosemide in a concentration of about 100 μM at about 4° C.;
    c) storing the heart by bathing it ex vivo in a cardioplegic solution comprising furosemide in a concentration of about 100 μM at about 4° C.; and
    d) perfusing the heart with a preservation solution at about 37° C. in order to remove the cardioplegic solution.

2. A method as set forth in claim 1 wherein the cardioplegic solution further comprises St. Thomas' Hospital cardioplegic solution of the formulation 110 mMNaCl, 16 mM KCl, 16 mMMgCl$_2$, 1.2 mM CaCl$_2$, 10 mM NaHCO$_3$.

\* \* \* \* \*